United States Patent
Wasicek (10) Patent No.: US 8,337,519 B2
(45) Date of Patent: Dec. 25, 2012

(54) EMBOLIC PROTECTION FILTERING DEVICE

(75) Inventor: Lawrence Wasicek, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2779 days.

(21) Appl. No.: 10/616,785

(22) Filed: Jul. 10, 2003

(65) Prior Publication Data

US 2005/0010245 A1    Jan. 13, 2005

(51) Int. Cl.
*A61M 29/00* (2006.01)

(52) U.S. Cl. ...................................... 606/200

(58) Field of Classification Search ............... 606/108, 606/159, 194, 200, 198; 604/96, 104, 105, 604/106

See application file for complete search history.

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 3,472,230 A | 10/1969 | Fogarty |
| 3,753,700 A | 8/1973 | Harrison et al. |
| 3,952,747 A | 4/1976 | Kimmell, Jr. |
| 3,996,938 A | 12/1976 | Clark, III |
| 4,046,150 A | 9/1977 | Schwartz et al. |
| 4,080,706 A | 3/1978 | Heilman et al. |
| 4,425,908 A | 1/1984 | Simon |
| 4,456,017 A | 6/1984 | Miles |
| 4,494,531 A | 1/1985 | Gianturco |
| 4,538,622 A | 9/1985 | Samson et al. |
| 4,590,938 A | 5/1986 | Segura et al. |
| 4,619,246 A | 10/1986 | Molgaard-Nielsen et al. |
| 4,650,466 A | 3/1987 | Luther |
| 4,688,553 A | 8/1987 | Metals |
| 4,706,671 A | 11/1987 | Weinrib |
| 4,723,549 A | 2/1988 | Wholey et al. |
| 4,763,647 A | 8/1988 | Gambale |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,813,434 A | 3/1989 | Buchbinder et al. |
| 4,846,186 A | 7/1989 | Box et al. |
| 4,873,978 A | 10/1989 | Ginsburg |
| 4,884,579 A | 12/1989 | Engelson |
| 4,921,478 A | 5/1990 | Solano et al. |
| 4,921,484 A | 5/1990 | Hillstead |
| 4,925,445 A | 5/1990 | Sakamoto et al. |

(Continued)

FOREIGN PATENT DOCUMENTS

DE    28 21 048    7/1980

(Continued)

OTHER PUBLICATIONS

U.S. Appl. No. 10/086,992, filed Apr. 10, 2003, Reynolds, Brian; et al.

(Continued)

*Primary Examiner* — Victor Nguyen

(74) *Attorney, Agent, or Firm* — Seager, Tufte & Wickhem LLC (57) ABSTRACT

Embolic protection devices and methods of making and using the same. An embolic protection device may include a shaft or filter wire having a filter coupled thereto. The filter wire may include a proximal section and a distal section. The proximal and distal sections may be coupled with a connector.

15 Claims, 6 Drawing Sheets

U.S. PATENT DOCUMENTS

| | | |
|---|---|---|
| 4,926,858 A | 5/1990 | Gifford, III et al. |
| 4,957,501 A | 9/1990 | Lahille et al. |
| 4,969,891 A | 11/1990 | Gewertz |
| 4,984,581 A | 1/1991 | Stice |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,063,935 A | 11/1991 | Gambale |
| 5,069,226 A | 12/1991 | Yamauchi et al. |
| 5,071,407 A | 12/1991 | Termin et al. |
| 5,100,423 A | 3/1992 | Fearnot |
| 5,102,415 A | 4/1992 | Guenther et al. |
| 5,109,867 A | 5/1992 | Twyford, Jr. |
| 5,111,829 A | 5/1992 | Alvarez de Toledo |
| 5,133,733 A | 7/1992 | Rasmussen et al. |
| 5,144,959 A | 9/1992 | Gambale et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,209,730 A | 5/1993 | Sullivan |
| 5,213,111 A | 5/1993 | Cook et al. |
| 5,224,953 A | 7/1993 | Morgentaler |
| 5,230,348 A | 7/1993 | Ishibe et al. |
| 5,238,004 A | 8/1993 | Sahatjian et al. |
| 5,253,653 A | 10/1993 | Daigle et al. |
| 5,271,415 A | 12/1993 | Foerster et al. |
| 5,273,052 A | 12/1993 | Kraus et al. |
| 5,275,173 A | 1/1994 | Samson et al. |
| 5,299,580 A | 4/1994 | Atkinson et al. |
| 5,312,356 A | 5/1994 | Engelson et al. |
| 5,313,967 A | 5/1994 | Lieber et al. |
| 5,329,942 A | 7/1994 | Gunther et al. |
| 5,330,484 A | 7/1994 | Gunther |
| 5,333,620 A | 8/1994 | Moutafis et al. |
| 5,341,818 A | 8/1994 | Abrams et al. |
| 5,345,945 A | 9/1994 | Hodgson et al. |
| 5,353,808 A | 10/1994 | Viera |
| 5,354,310 A | 10/1994 | Garnie et al. |
| 5,365,943 A | 11/1994 | Jansen |
| 5,368,048 A | 11/1994 | Stoy et al. |
| 5,376,100 A | 12/1994 | Lefebvre |
| 5,383,887 A | 1/1995 | Nadal |
| 5,406,960 A | 4/1995 | Corso, Jr. |
| 5,411,476 A | 5/1995 | Abrams et al. |
| 5,421,832 A | 6/1995 | Lefebvre |
| 5,423,742 A | 6/1995 | Theron |
| 5,433,200 A | 7/1995 | Fleischhacker, Jr. |
| 5,443,907 A | 8/1995 | Slaikeu et al. |
| 5,449,372 A | 9/1995 | Schmaltz et al. |
| 5,452,726 A | 9/1995 | Burmeister et al. |
| 4,842,579 B1 | 10/1995 | Shiber |
| 5,456,667 A | 10/1995 | Ham et al. |
| 5,462,529 A | 10/1995 | Simpson et al. |
| 5,465,732 A | 11/1995 | Abele |
| 5,479,938 A | 1/1996 | Weier |
| 5,536,242 A | 7/1996 | Willard et al. |
| 5,549,626 A | 8/1996 | Miller et al. |
| 5,606,981 A | 3/1997 | Tartacower et al. |
| 5,637,089 A | 6/1997 | Abrams et al. |
| 5,651,373 A | 7/1997 | Mah |
| 5,658,296 A | 8/1997 | Bates et al. |
| 5,662,671 A | 9/1997 | Barbut et al. |
| 5,695,111 A | 12/1997 | Nanis et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,749,848 A | 5/1998 | Jang et al. |
| 5,769,796 A | 6/1998 | Palermo et al. |
| 5,769,816 A | 6/1998 | Barbut et al. |
| 5,772,609 A | 6/1998 | Nguyen et al. |
| 5,772,641 A | 6/1998 | Wilson |
| 5,776,100 A | 7/1998 | Forman |
| 5,779,716 A | 7/1998 | Cano et al. |
| 5,782,776 A | 7/1998 | Hani |
| 5,792,157 A | 8/1998 | Mische et al. |
| 5,795,322 A | 8/1998 | Bouewijn |
| 5,797,857 A | 8/1998 | Obitsu |
| 5,800,457 A | 9/1998 | Gelbfish |
| 5,800,525 A | 9/1998 | Bachinski et al. |
| 5,810,874 A | 9/1998 | Lefebvre |
| 5,813,996 A | 9/1998 | St. Germain et al. |
| 5,814,064 A * | 9/1998 | Daniel et al. .................. 606/200 |
| 5,820,571 A | 10/1998 | Erades et al. |
| 5,827,324 A | 10/1998 | Cassell et al. |
| 5,833,631 A | 11/1998 | Nguyen |
| 5,833,644 A | 11/1998 | Zadno-Azizi et al. |
| 5,833,650 A | 11/1998 | Imran |
| 5,836,892 A | 11/1998 | Lorenzo |
| 5,836,893 A | 11/1998 | Urick |
| 5,836,968 A | 11/1998 | Simon et al. |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,471 A | 11/1999 | Jafari |
| 5,980,555 A | 11/1999 | Barbut et al. |
| 5,984,878 A | 11/1999 | Engelson |
| 5,989,281 A | 11/1999 | Barbut et al. |
| 5,993,469 A | 11/1999 | McKenzie et al. |
| 5,997,557 A | 12/1999 | Barbut et al. |
| 6,001,068 A | 12/1999 | Uchino et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,013,854 A * | 1/2000 | Moriuchi ..................... 623/1.11 |
| 6,027,520 A | 2/2000 | Tsugita et al. |
| 6,029,671 A * | 2/2000 | Stevens et al. ................ 128/898 |
| 6,039,699 A | 3/2000 | Viera |
| 6,042,553 A | 3/2000 | Solar et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,106,488 A | 8/2000 | Fleming et al. |
| 6,117,154 A | 9/2000 | Barbut et al. |
| 6,129,739 A | 10/2000 | Khosravi |
| 6,136,016 A | 10/2000 | Barbut et al. |
| 6,139,510 A | 10/2000 | Palermo |
| 6,142,987 A | 11/2000 | Tsugita |
| 6,152,946 A | 11/2000 | Broome et al. |
| 6,165,200 A | 12/2000 | Tsugita et al. |
| 6,165,292 A | 12/2000 | Abrams et al. |
| 6,168,571 B1 | 1/2001 | Solar et al. |
| 6,168,579 B1 | 1/2001 | Tsugita |
| 6,171,327 B1 * | 1/2001 | Daniel et al. .................. 606/200 |
| 6,171,328 B1 | 1/2001 | Addis |
| 6,179,788 B1 | 1/2001 | Sullivan |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,183,420 B1 | 2/2001 | Douk et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,234,981 B1 | 5/2001 | Howland |
| 6,235,044 B1 | 5/2001 | Root et al. |

| | | | | | | | |
|---|---|---|---|---|---|---|---|
| 6,235,045 | B1 | 5/2001 | Barbut et al. | WO | WO 92/03097 | 3/1992 | |
| 6,238,412 | B1 | 5/2001 | Dubrul et al. | WO | WO 94/14389 | 7/1994 | |
| 6,245,087 | B1 | 6/2001 | Addis | WO | WO 94/24946 | 11/1994 | |
| 6,245,088 | B1 | 6/2001 | Lowery | WO | WO 96/01591 | 1/1996 | |
| 6,245,089 | B1 | 6/2001 | Daniel et al. | WO | WO 96/10375 | 4/1996 | |
| 6,248,082 | B1 | 6/2001 | Jafari | WO | WO 96/19941 | 7/1996 | |
| 6,258,115 | B1 | 7/2001 | Dubrul | WO | WO 96/23441 | 8/1996 | |
| 6,264,663 | B1 | 7/2001 | Cano | WO | WO 96/33677 | 10/1996 | |
| 6,264,672 | B1 | 7/2001 | Fisher | WO | WO 97/17100 | 5/1997 | |
| 6,270,513 | B1 | 8/2001 | Tsugita et al. | WO | WO 97/27808 | 8/1997 | |
| 6,277,138 | B1 | 8/2001 | Levinson et al. | WO | WO 97/42879 | 11/1997 | |
| 6,277,139 | B1 | 8/2001 | Levinson et al. | WO | WO 98/02084 | 1/1998 | |
| 6,280,413 | B1 | 8/2001 | Clark et al. | WO | WO 98/02112 | 1/1998 | |
| 6,287,321 | B1 | 9/2001 | Jang | WO | WO 98/23322 | 6/1998 | |
| 6,290,710 | B1 | 9/2001 | Cryer et al. | WO | WO 98/33443 | 8/1998 | |
| 6,306,105 | B1 | 10/2001 | Rooney et al. | WO | WO 98/34673 | 8/1998 | |
| 6,309,399 | B1 | 10/2001 | Barbut et al. | WO | WO 98/36786 | 8/1998 | |
| 6,319,268 | B1 | 11/2001 | Ambrisco et al. | WO | WO 98/38920 | 9/1998 | |
| 6,319,510 | B1 | 11/2001 | Yates | WO | WO 98/38929 | 9/1998 | |
| 6,336,934 | B1 * | 1/2002 | Gilson et al. ............ 606/200 | WO | WO 98/39046 | 9/1998 | |
| 6,344,049 | B1 | 2/2002 | Levinson et al. | WO | WO 98/39053 | 9/1998 | |
| 6,346,116 | B1 | 2/2002 | Brooks et al. | WO | WO 98/46297 | 10/1998 | |
| 6,352,515 | B1 | 3/2002 | Anderson et al. | WO | WO 98/47447 | 10/1998 | |
| 6,428,559 | B1 | 8/2002 | Johnson | WO | WO 98/49952 | 11/1998 | |
| 6,432,122 | B1 | 8/2002 | Gilson et al. | WO | WO 98/50103 | 11/1998 | |
| 6,443,972 | B1 | 9/2002 | Bosma et al. | WO | WO 98/51237 | 11/1998 | |
| 6,461,370 | B1 * | 10/2002 | Gray et al. ............ 606/200 | WO | WO 98/55175 | 12/1998 | |
| 6,482,222 | B1 | 11/2002 | Bruckheimer et al. | WO | WO 99/09895 | 3/1999 | |
| 6,485,502 | B2 | 11/2002 | Don Michael et al. | WO | WO 99/22673 | 5/1999 | |
| 6,488,637 | B1 | 12/2002 | Eder et al. | WO | WO 99/23976 | 5/1999 | |
| 6,506,205 | B2 | 1/2003 | Goldberg et al. | WO | WO 99/25252 | 5/1999 | |
| 6,508,803 | B1 | 1/2003 | Horikawa et al. | WO | WO 99/30766 | 6/1999 | |
| 6,511,496 | B1 | 1/2003 | Huter et al. | WO | WO 99/40964 | 8/1999 | |
| 6,511,497 | B1 | 1/2003 | Braun et al. | WO | WO 99/42059 | 8/1999 | |
| 6,540,722 | B1 | 4/2003 | Boyle et al. | WO | WO 99/44510 | 9/1999 | |
| 6,551,342 | B1 | 4/2003 | Shen et al. | WO | WO 99/44542 | 9/1999 | |
| 6,558,405 | B1 | 5/2003 | McInnes | WO | WO 99/55236 | 11/1999 | |
| 6,569,183 | B1 | 5/2003 | Kim et al. | WO | WO 99/58068 | 11/1999 | |
| 6,575,996 | B1 | 6/2003 | Denison et al. | WO | WO 00/07521 | 2/2000 | |
| 2002/0052626 | A1 | 5/2002 | Gilson et al. | WO | WO 00/07655 | 2/2000 | |
| 2002/0091409 | A1 | 7/2002 | Sutton et al. | WO | WO 00/09054 | 2/2000 | |
| | FOREIGN PATENT DOCUMENTS | | | WO | WO 00/16705 | 3/2000 | |
| DE | 34 17 738 | | 11/1985 | WO | WO00/40286 | 7/2000 | |
| DE | 40 30 998 | A1 | 10/1990 | WO | WO 00/49970 | 8/2000 | |
| DE | 199 16 162 | | 10/2000 | WO | WO 00/53120 | 9/2000 | |
| EP | 0 200 688 | | 11/1986 | WO | WO 00/67664 | 11/2000 | |
| EP | 0 274 412 | | 7/1988 | WO | WO 00/67665 | 11/2000 | |
| EP | 0 293 605 | A1 | 12/1988 | WO | WO 00/67666 | 11/2000 | |
| EP | 0 350 043 | | 1/1991 | WO | WO 00/67668 | 11/2000 | |
| EP | 0 411 118 | A1 | 2/1991 | WO | WO 00/67669 | 11/2000 | |
| EP | 0 427 429 | A2 | 5/1991 | WO | WO 01/05462 | 1/2001 | |
| EP | 0 437 121 | B1 | 7/1991 | WO | WO 01/08595 | 2/2001 | |
| EP | 0 472 334 | A1 | 2/1992 | WO | WO 01/08596 | 2/2001 | |
| EP | 0 472 368 | A2 | 2/1992 | WO | WO 01/08742 | 2/2001 | |
| EP | 0 491 349 | | 6/1992 | WO | WO 01/08743 | 2/2001 | |
| EP | 0 533 511 | A1 | 3/1993 | WO | WO 01/10320 | 2/2001 | |
| EP | 0 655 228 | A1 | 11/1994 | WO | WO 01/15629 | 3/2001 | |
| EP | 0 686 379 | A2 | 6/1995 | WO | WO 01/21077 | 3/2001 | |
| EP | 0 696 447 | A2 | 2/1996 | WO | WO 01/21100 | 3/2001 | |
| EP | 0 737 450 | A1 | 10/1996 | WO | WO 01/26726 | 4/2001 | |
| EP | 0 743 046 | A1 | 11/1996 | WO | WO 01/35857 | 5/2001 | |
| EP | 0 759 287 | A1 | 2/1997 | WO | WO 01/43662 | 6/2001 | |
| EP | 0 771 549 | A2 | 5/1997 | WO | WO 01/47579 | 7/2001 | |
| EP | 0 784 988 | A1 | 7/1997 | WO | WO 01/49208 | 7/2001 | |
| EP | 0 806 220 | | 11/1997 | WO | WO 01/49209 | 7/2001 | |
| EP | 0 838 230 | | 4/1998 | WO | WO 01/49215 | 7/2001 | |
| EP | 0 852 132 | A1 | 7/1998 | WO | WO 01/49355 | 7/2001 | |
| EP | 0 934 729 | | 8/1999 | WO | WO 01/52768 | 7/2001 | |
| EP | 1 127 556 | A2 | 8/2001 | WO | WO 01/58382 | 8/2001 | |
| FR | 2 580 504 | | 10/1986 | WO | WO 01/60442 | 8/2001 | |
| FR | 2 643 250 | A1 | 8/1990 | WO | WO 01//67989 | 9/2001 | |
| FR | 2 666 980 | | 3/1992 | WO | WO 01/70326 | 9/2001 | |
| FR | 2 694 687 | | 8/1992 | WO | WO 01/72205 | 10/2001 | |
| FR | 2 768 326 | A1 | 3/1999 | WO | WO 01/87183 | 11/2001 | |
| GB | 2 020 557 | B | 1/1983 | WO | WO 01/89413 | 11/2001 | |
| JP | 8-187294 | A | 7/1996 | WO | WO 2004/054652 | 7/2004 | |
| SU | 764684 | | 9/1980 | | | | |
| WO | WO 88/09683 | | 12/1988 | | | | |

OTHER PUBLICATIONS

U.S. Appl. No. 10/375,766, filed Feb. 26, 2003, Reynolds, Brian; et al.

U.S. Appl. No. 09/972,276, filed Oct. 5, 2001, Peter Skujins et al.

"Atherosclerotic Disease of the Aortic Arch as a Risk Factor of Recurrent Ischemic Stroke," *The New England Journal of Medicine*, pp. 1216-1221 (May 1996).

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

EMBOLIC PROTECTION FILTERING DEVICE

FIELD OF THE INVENTION

The invention pertains to embolic protection filtering devices. More particularly, the invention pertains to embolic protection filtering devices with an improved filter wire.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action. In addition, blockages in cranial areas or in vessels adjacent the brain could lead to considerable complications such as stroke.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

Typically, embolic protection filtering devices include a filter attached to a shaft or filter wire. Because the vasculature of a patient may be very tortuous, it may be desirable to combine a number of performance features into the filter wire. For example, it is sometimes desirable that the filter wire have a relatively high level of pushability and torqueability, particularly near its proximal end. It is also sometimes desirable that the filter wire be relatively flexible, particularly near its distal end. A number of different filter wire structures and assemblies are known, each having certain advantages and disadvantages. However, there is an ongoing need to provide alternative filter wire structures and assemblies.

BRIEF SUMMARY

The invention pertains to embolic protection filtering devices. In at least some embodiments, an embolic protection filtering device includes an elongate shaft or filter wire having a filter coupled thereto. The filter wire may include a first section, a second section, and a connector assembly connecting the first and second sections. Some of the other structural features and characteristics are described in more detail below. The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

When a clinician performs an intravascular intervention such as angioplasty, atherectomy, and the like, embolic debris may dislodge from the blood vessel that can travel in the bloodstream to a position where it may impair blood flow, possibly leading to tissue damage. A number of other situations and/or interventions may also result in the mobilization of embolic debris. Accordingly, embolic protection filtering devices have been developed that can be disposed in the blood vessel downstream of the treatment site and expanded to capture debris.

Figure 1:
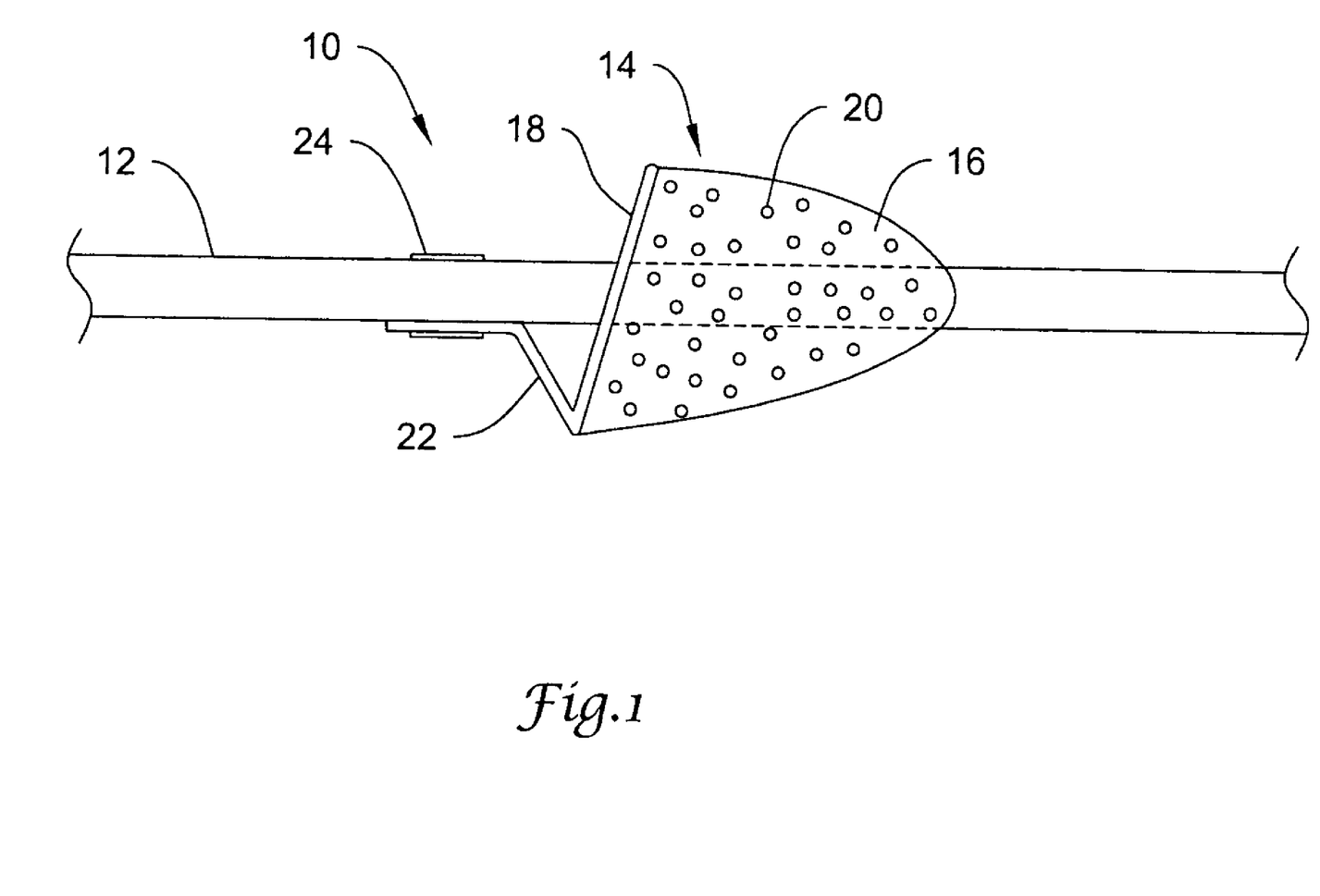
FIG. 1 is a partial side view of an example medical device.

FIG. 1 illustrates an example embolic protection filtering device 10 that can be used to filter embolic debris. Filtering device 10 includes an elongate shaft 12 having an embolic protection filter 14 coupled thereto. In some embodiments, shaft 12 can be a guidewire or filter wire. Some of the features and characteristics of suitable filter wires are described in more detail below. However, shaft 12 may include any suitable medical device such as a catheter (e.g., therapeutic, diagnostic, or guide catheter), endoscopic device, laproscopic device, or any other suitable device. Additionally, in other embodiments, shaft 12 may be a tubular filter cartridge configured to be slidable over a guidewire, filter wire, or other medical device.

Filter 14 may include a filter membrane or material 16 coupled to a filter frame or loop 18. Filter material 16 can be drilled (for example, formed by known laser techniques) or otherwise manufactured to include a plurality of openings 20. The holes or openings 20 are sized to allow blood flow therethrough but restrict flow of debris or embolic floating in the body lumen or cavity. Filter 14 and/or frame 18 may be adapted to operate between a first generally collapsed configuration and a second generally expanded configuration for collecting debris in a body lumen. Shifting between the expanded and collapsed configuration may be accomplished in a number of ways. For example, frame 18 may include a shape-memory material such as nickel-titanium alloy that may render frame 18 "self-expanding" (to bias filter 14 to be in the second expanded configuration). Accordingly, filter 14 can be collapsed in a suitable delivery device and advanced through the vasculature to the desired location. The delivery device can then be proximally retracted so that filter 14 emerges from the distal end of the delivery device and expands. It can be appreciated that a number of different materials can be used to manufacture filter 14 such as metals, metal alloys, and polymers such as those listed below. Additionally, frame 18 may include a radiopaque material or include, for example, a radiopaque wire disposed about a portion thereof.

One or more struts 22 may extend between frame 18 and shaft or filter wire 12 and be coupled to filter wire 12 by a coupling 24. Coupling 24 may be one or more windings of struts 22 about filter wire 12 or be a fitting disposed over an end of struts 22 to attach it to filter wire 12. It can be appreciated that in embodiments where shaft 12 comprises a tubular filter cartridge, struts 22 would extend between frame 18 and the filter cartridge.

Figure 2:
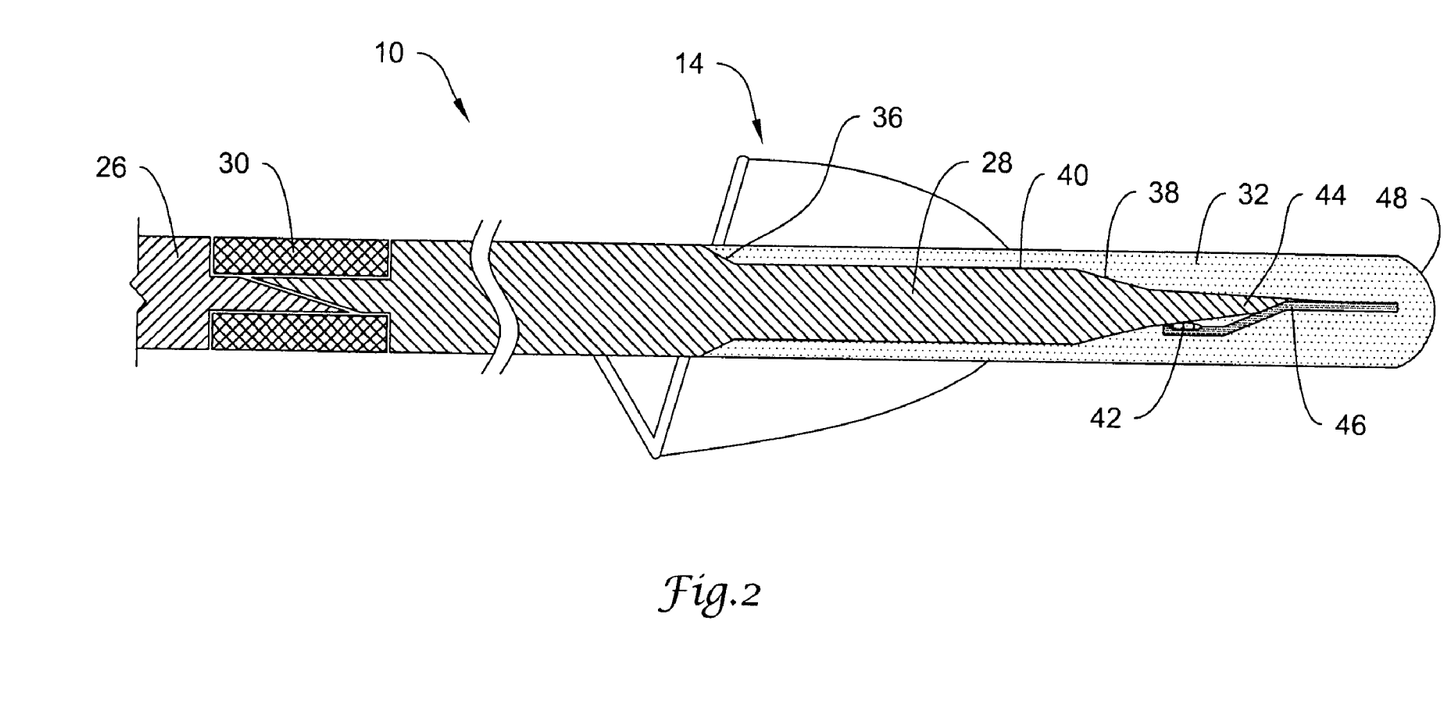
FIG. 2 is a partial cross-sectional view of an example medical device.

A partial cross-sectional side view of device 10 is shown in FIG. 2. Here it can be seen that shaft or filter wire 12 may include a proximal section 26, a distal section 28, a connector 30 for coupling proximal and distal sections 26/28, and a covering or sheath 32. Proximal and distal sections 26/28 may have a solid cross-section as shown, or a hollow cross-section, and may be formed of any materials suitable for use, dependent upon the desired properties of the guidewire. In some embodiments, proximal section 26 may include a relatively stiff material, for example stainless steel such as 304V, 304L, and 316L stainless steel, or the like, or other suitable materials. Alternatively, proximal section 26 may include another metal or metal alloy, for example a nickel-titanium alloy such as a superelastic (i.e. pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or other suitable metals, or combinations or alloys thereof; or the like; or a polymer material such as a high performance polymer. In general, the material used to construct proximal section 26 may be selected to be relatively stiff for pushability and torqueability. However, other embodiments are contemplated.

In some embodiments, distal section 28 may be formed of a relatively flexible material such as a super elastic or linear elastic alloy (e.g., nickel-titanium) wire, or alternatively, a polymer material, such as a high performance polymer. Alternatively, distal section 28 may include a metal or metal alloy including any of those listed above, other suitable metals, combinations or alloys thereof, or the like, or other suitable materials. In general, the material used to construct distal section 28 may be selected to be relatively flexible for trackability. However, other embodiments are contemplated.

In some particular embodiments, proximal section 26 and/or distal section 28 may include nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiment, the range of weight percent nickel and titanium, and or other trace elements may vary from these ranges. Within the family of commercially available nitinol alloys, are categories designated as "superelastic" (i.e. pseudoelastic) and "linear elastic" which, although similar in chemistry, exhibits distinct and useful mechanical properties.

In some embodiments, a superelastic alloy, for example a superelastic nitinol can be used to achieve desired properties. Such alloys typically display a substantial "superelastic plateau" or "flag region" in its stress/strain curve. Such alloys can be desirable in some embodiments because a suitable superelastic alloy will provide a portion of the shaft 12 that exhibits some enhanced ability, relative to some other non-superlastic materials, of substantially recovering its shape without significant plastic deformation, upon the application and release of stress, for example, during placement of the catheter in the body.

In some other embodiments, a linear elastic alloy, for example a linear elastic nitinol can be used to achieve desired properties. For example, in some embodiments, certain linear elastic nitinol alloys can be generated by the application of cold work, directional stress, and heat treatment, such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there is no martensite/austenite phase changes detectable by DSC and DMTA analysis in the range of about −60° C. to about 120° C., and in other embodiments, in the range of about −100° C. to about 100° C. The mechanical bending properties of such material are therefore generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy allows the shaft to exhibit superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

Proximal section 26 and/or distal section 28 may include one or more tapered regions. For example, distal section 28 may include tapered regions 36 and 38. Between tapered regions 36/38 there may be a constant diameter region 40. Of course, the number of tapered regions and constant diameter regions is not intended to be limited to what is shown as any appropriate numbers of such structures may be used. An end portion 44 may also be defined that has a geometry that generally decreases in cross sectional area toward the distal end thereof. In some embodiments, these tapers 36/38 and/or constant diameter region 40 are adapted and/or configured to obtain a transition in stiffness, and provide a desired flexibility characteristic. Formation of tapers 36/38 may include typical grinding protocols such as those described below. A wire or ribbon 46 May be disposed adjacent distal section 28 (e.g., coupled to distal section 28 at bond 42), and extend distally of end portion 44. In some embodiments, wire or ribbon 46 can be a fabricated or formed wire structure, for example a coiled wires, as will be seen in embodiments discussed in more detail below. In some embodiments, wire or ribbon 46 can function as a shaping structure or a safety structure.

It will be understood by those of skill in the art and others that a broad variety of materials, dimensions, and structures can be used to construct suitable embodiments, depending upon the desired characteristics. The following examples of some dimensions are included by way of example only, and are not intended to be limiting. In some embodiments, proximal section 26 may have a diameter in the range of 0.01 to 0.05 inches and a length in the range of about 50 to about 190 inches. Distal section 28 may have a diameter that ranges from about 0.02 to about 0.002 inches or so, and a length in the range of 3 to 40 inches. Constant diameter region 40 may have an outer diameter in the range of about 0.001 to about 0.02 inches. Constant diameter region 40 may have a length in the range of about 0.5 to about 25 inches. Tapered regions 36/38 may each have lengths in the range of about 0.5 to about 2 inches or so and may vary from each other. Some other examples of dimensions, materials, and configurations for device 10, shaft 12, and the various components thereof can be found in U.S. patent application Ser. No. 10/086,992 entitled "Composite Guidewire", filed on Feb. 28, 2002, which is incorporated herein by reference.

Figure 9:
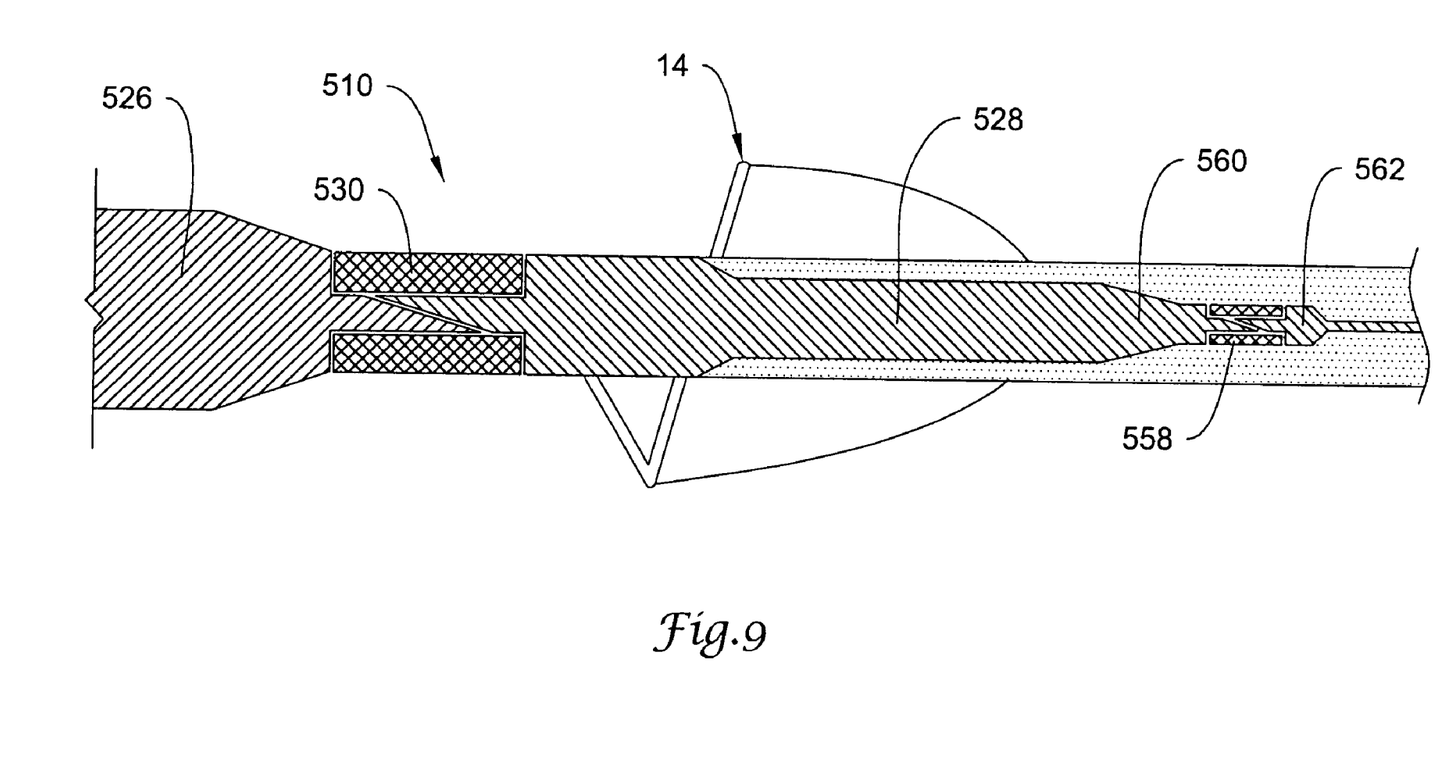
FIG. 9 is a partial cross-sectional view of another example medical device.

Although FIG. 2 depicts filter 14 as being coupled to filter wire 12 at distal section 28, this need not be the case as filter 14 can be disposed at essentially any position along filter wire 12. The position of filter 14 relative to connector 30 may also vary. For example, FIG. 2 depicts filter 14 being disposed distally of connector 30. However, filter 14 may be disposed proximally of connector without departing from the spirit of the invention. Moreover, some embodiments of filter wire 12 may include more than one connector 30 (e.g., device 510 as illustrated in FIG. 9) so that filter 12 may be disposed between two connectors 30. Additionally, some embodiments may include more than one filter 14.

The form of sheath or covering 32 may also vary. For example, FIG. 2 depicts covering 32 as being a polymer sheath disposed over a portion of distal section 28. In other embodiments, other structures, for example a helical coil or spring tip may be used, for example, as discussed below. In the embodiment shown, sheath 32 extends from about tapered region 36 to beyond end portion 44 and forms a rounded tip 48. In other embodiments, sheath 32 can extend further in a proximal direction, and in some cases can extend over connector 30, or over proximal section 26. In yet other embodiments, sheath 32 can begin at a point distal of tapered region 36.

Material for use as the sheath 32 include any material that would give the desired strength, flexibility or other desired characteristics. Some suitable materials include polymers, and like material. Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments sheath 32 can be blended with a liquid crystal polymer (LCP). For example, the mixture can contain up to about 5% LCP. This has been found to enhance torqueability. By employing selection of materials and processing techniques, thermoplastic, solvent soluble, and thermosetting variants of these and other materials can be employed to achieve the desired results.

The use of a polymer for sheath 32 can serve several functions. The use of a polymer can improve the flexibility properties of distal section 28. Choice of polymers for sheath 32 will vary the flexibility. For example, polymers with a low durometer or hardness will make a very flexible or floppy tip. Conversely, polymers with a high durometer will make a tip which is stiffer. The use of polymers for the sleeve can also provide a more atraumatic tip for shaft 12. An atraumatic tip is better suited for passing through fragile body passages. Finally, a polymer can act as a binder for radiopaque materials, which may aid in the visualization of shaft 12.

Sheath 32 can be disposed around and attached to shaft 12 using any suitable technique for the particular material used. In some embodiments, sheath 32 is attached by heating a sleeve of polymer material to a temperature until it is reformed around the distal section 28 (and ribbon 46). In some other embodiments, sheath 32 can be attached using heat shrinking, extrusion, adhesive bonding, a mechanical fitting or interlocking, or other suitable techniques. Sheath 32 may be finished, for example, by a centerless grinding or other method, to provide the desired diameter and to provide a smooth outer surface.

In some embodiments, sheath 32, or portions thereof, can include, or be doped with, radiopaque material to make sheath 32, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, sheath 32 can include different sections having different amounts of loading with radiopaque material. In some embodiments, it is also contemplated that a separate radiopaque member or a series of radiopaque members, such as radiopaque coils, bands, tubes, or other such structures could be attached to shaft 12 or sheath 32, or portions thereof, or incorporated into it by plating, drawing, forging, or ion implantation techniques.

Additionally, in some embodiments, a coating, for example a lubricious (e.g., hydrophylic) or other type of coating may be applied over portions or all of sheath 32, and/or other portions of shaft 12. Hydrophobic coatings such as fluoropolymers provide a dry lubricity which improves the handling of shaft 12 and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, distal section 28 may be coated with a hydrophilic polymer as discussed above, and proximal section 26 may be coated with a fluoropolymer, such as polytetrafluroethylene (PTFE).

Figure 3:
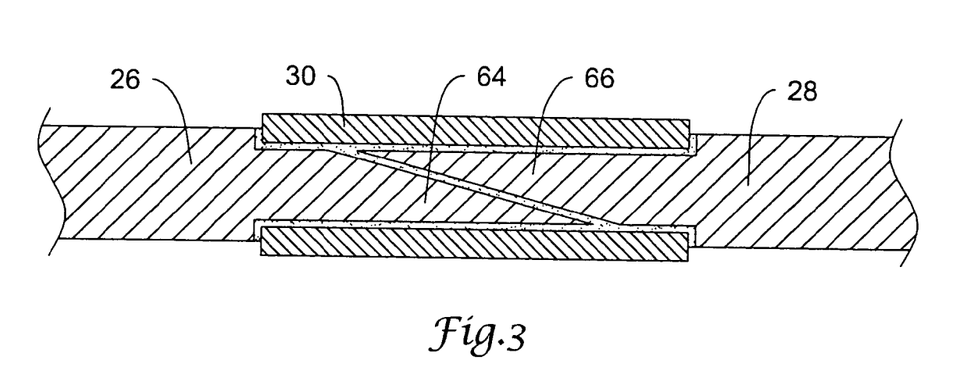
FIG. 3 is a cross-sectional view of the connection of a proximal section and distal section of an example filter wire.

FIG. 3 illustrates a cross-sectional side view of connector 30, connecting proximal section 26 and distal section 28. Connector 30 may comprise a tubular structure such as a hypotube as shown, a coiled wire, or any other suitable structure. Connector may have an inside diameter sized appropriately to receive the distal end 64 of proximal portion 26 and the proximal end 66 of distal portion 28, and can have an outside diameter sufficient to accommodate a final grinding procedure. It should be understood by those of skill in the art and others that a broad variety of materials, dimensions, and structures can be used for connector 30, dependent upon the desired characteristics and structures being connected. The following examples of some dimensions and materials, therefore, are included by way of example only, and are not intended to be limiting. In some example embodiments, connector 30 can have an inner diameter in the range of about 0.005 to about 0.02 inches, and an outer diameter in the range of about 0.01 to about 0.025 inches. In some particular embodiments, connector 30 can have and inner diameter of about 0.010 inches and an outer diameter of about 0.014 inches. The final diameter of filter wire 12 and connector 30 may be in the range of 0.010 to 0.018 inches, for example. Connector 30 may have a length of about 1.0 to 3.0 inches. However, in some other embodiments, this type of construction can be applied to wires of larger diameter intended, for example, for peripheral intervention purposes. Such wires could range as large as 0.035 or larger in diameter and therefore have an extended length connector and correspondingly longer overlapping sections.

Connector 30 may include a metal or metal alloy, and may include radiopaque materials. Suitable metals and metal alloys include stainless steels, nickel-titanium alloys (e.g., nitinol), nickel-chromium alloys, nickel-chromium-iron alloys, cobalt alloys, nickel, or other suitable materials. Alternatively, connector 30 may include a polymer or a metal-polymer composite, including a radiopaque filler. Some types of alloys are particularly suitable for connector 30 for purposes of connecting a stainless steel proximal section 26 and a nickel titanium alloy distal section 28, or visa-versa. An example is a nickel-chromium-iron alloy designated UNS N06625 and is available under the trade name INCONEL 625, which advantageously welds to both stainless steels and nickel-titanium alloys. INCONEL 625 wire may be obtained from California Fine Wire Company of Grover Beach, Calif., and has the following typical composition:

| Material | Symbol | % by wgt |
|---|---|---|
| Aluminum | Al | 0.140 |
| Carbon | C | 0.070 |
| Chromium | Cr | 21.900 |
| Cobalt | Co | 0.010 |
| Copper | Cu | 0.030 |
| Iron | Fe | 2.790 |
| Manganese | Mn | 0.030 |
| Molybdenum | Mo | 9.150 |
| Nickel | Ni | 62.000 |
| Niobium | Nb | 3.540 |
| Phosphorus | P | 0.005 |
| Silicon | Si | 0.230 |
| Sulfur | S | 0.009 |
| Titanium | Ti | 0.250 |
| Tantalum | Ta | 0.010 |

Another example of a suitable alloy which welds to both stainless steels and nickel-titanium alloys is designated UNS 10276 and is available under the trade name ALLOY C276 from Fort Wayne Metals Research Products Corporation of Fort Wayne, Ind., which has the following typical composition:

| Material | Symbol | % by wgt |
|---|---|---|
| Carbon | C | 0.003 |
| Chromium | Cr | 15.810 |
| Cobalt | Co | 1.310 |
| Copper | Cu | 0.100 |
| Iron | Fe | 5.730 |
| Manganese | Mn | 0.520 |
| Molybdenum | Mo | 16.010 |
| Nickel | Ni | 57.000 |
| Phosphorus | P | 0.008 |
| Silicon | Si | 0.020 |
| Sulfur | S | 0.005 |
| Tungsten | W | 3.570 |
| Vanadium | V | 0.160 |

Another example of a suitable alloy which welds to both stainless steels and nickel-titanium alloys is of the Hastelloy family and an example of which is available under the trade name ALLOY B2 from Fort Wayne Metals Research Products Corporation of Fort Wayne, Ind., which has the following typical composition:

| Material | Symbol | % by wgt |
|---|---|---|
| Carbon | C | 0.005 |
| Chromium | Cr | 0.450 |
| Cobalt | Co | 0.110 |
| Copper | Cu | 0.030 |
| Iron | Fe | 1.410 |
| Manganese | Mn | 0.150 |
| Molybdenum | Mo | 27.720 |
| Nickel | Ni | 70.000 |
| Phosphorus | P | 0.004 |
| Silicon | Si | 0.020 |
| Sulfur | S | 0.002 |
| Tungsten | W | 0.140 |

Figure 4:
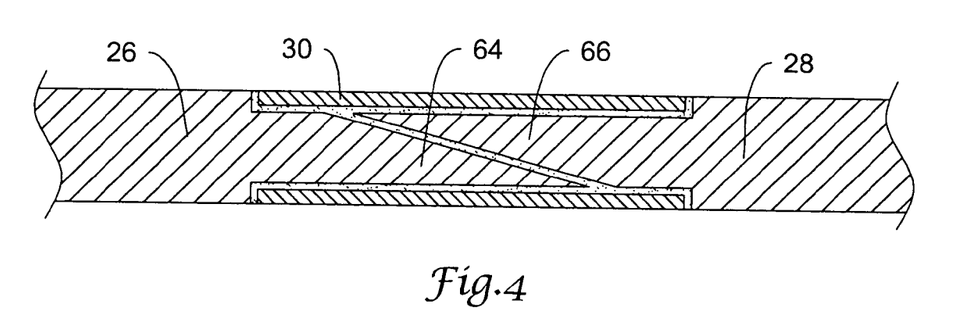
FIG. 4 is another cross-sectional view of the connection of a proximal section and distal section of an example filter wire.

To manufacture filter wire 12, the ends 64/66 of the proximal and distal guidewire 26/28 may be ground to form a desired shape. For example, FIGS. 3 and 4 illustrate that ends 64/66 may be ground to include a taper. In the tapered embodiments illustrated in FIGS. 2-4, the ends 64/66 may be tapered or otherwise formed to have a mating geometry that gradually decreases in cross sectional area toward the middle of connector 30. The tapered overlapping portion may define a uniform or a non-uniform transition of the sections 26/28, depending on the transition characteristics desired. For example, the end sections 26/28 may be linearly tapered as shown, tapered in a curvilinear fashion, or tapered in a stepwise fashion. If tapered linearly as shown, the angle of the taper may vary. Using the longitudinal center axis of filter wire 12 as a reference, as measured from the extreme ends of the end sections 64/66, the angle of the taper is acute (i.e., less than 90 degrees), and may be in the range of 5 degrees to 45 degrees, for example. Varying the angle of the tapered ends 64/66 also varies the length of the overlapping joint in accordance with geometric principles. The length of the overlapping joint may be selected to obtain a more (longer length) or less (shorter length) gradual transition in stiffness.

This tapered arrangement may be desirable, for example, by allowing the flexibilities of proximal section 26 and distal section 28 to be blended. For example, proximal section 26 may comprise a first material having a first flexibility and distal section 28 may comprise a second (differing) material having a second flexibility. By overlapping ends 64/66 the differing flexibilities, the transition between flexibility can be made to be more gradual. The overlapping joint, thus, blends the stiffness of proximal section 26 and distal section 28 by combining the properties of each end section 64/66 making up the cross section of the overlapping joint. Thus, the joint forms a flexibility transition region that has a relative flexibility that is between the flexibility of the proximal section 26 and the flexibility of the distal section 28.

To assemble filter wire 12, connector 30 can be positioned over the ends 64/66 of the proximal and distal sections 26/28 as shown in FIG. 3. The proximal and distal sections 26/28 and connector 30 may be bonded, welded (e.g., resistance or laser welded), soldered, brazed, or otherwise connected by a suitable technique depending on the material selected for each component. It is to be appreciated that various welding processes may be utilized without deviating from the spirit and scope of the present invention. Examples of welding processes which may be suitable in some applications include LASER welding, resistance welding, TIG welding, microplasma welding, electron beam, and friction or inertia welding. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn. Alternatively, the ends 64/66 and connector 30 may be crimped together or may be sized to establish a mechanical connection, such as an interlocking or friction fit therebetween.

Once connected, connector 30 and proximal and distal sections 26/28 can be finished, for example, through centerless grinding to provide a smooth and uniform profile across connector 30 as shown in FIG. 4, and to straighten out small misalignments between proximal and distal sections 26/28. Other portions of filter wire 12 may be ground as well to provide the desired tapers and changes in diameter. Once finally ground, in some embodiments, a flexible coil tip and/or a polymer jacket tip or combination thereof, and other such structure, such as radiopaque markers, safety and/or shaping ribbons (coiled or uncoiled), and the like, may be placed on filter wire 12. Additionally, in some embodiments, a coating, for example a lubricious (e.g., hydrophilic) or other type of coating may be applied to all or portions of filter wire 12 including those described above.

The centerless grinding technique may utilize an indexing system employing sensors (e.g., optical/reflective, magnetic) to avoid excessive grinding of connector 30. In some embodiments, the presence of dissimilar materials in the construction can influence the grinding technique and tooling used to accomplish uniform material removal, create smooth transitions, and successfully bridge across adjacent components. In addition, the centerless grinding technique may utilize a CBN or diamond abrasive grinding wheel that is well shaped and dressed to avoid grabbing connector 30 during the grinding process.

Figure 5:
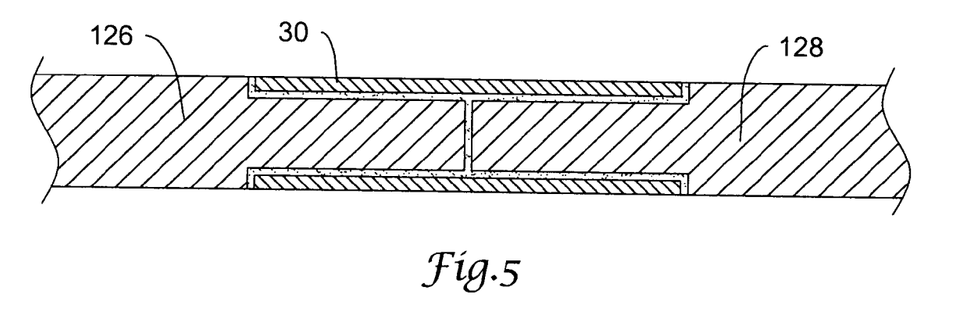
FIG. 5 is another cross-sectional view of the connection of a proximal section and distal section of an example filter wire.
Figure 6:
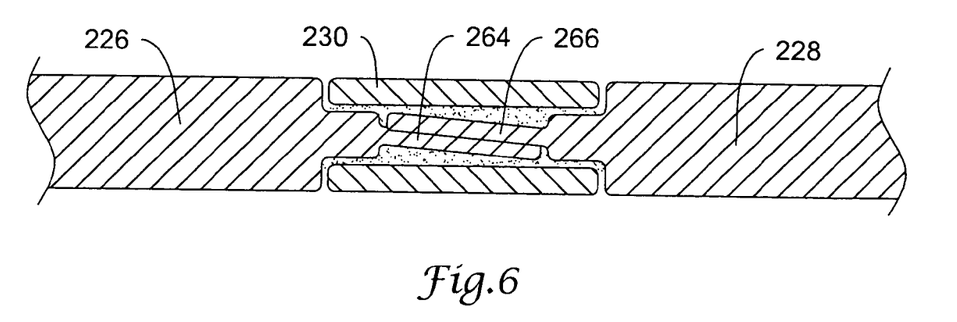
FIG. 6 is another cross-sectional view of the connection of a proximal section and distal section of an example filter wire.

The embodiment of FIG. 5 is similar to the embodiment of FIGS. 3 and 4, except that connector 130 between proximal section 126 and distal section 128 does not utilize an overlapping joint, but rather uses a butt joint. The embodiment of FIG. 6 is also similar to the previously shown embodiments, except that connector 230 between proximal section 226 and distal section 228 utilizes an overlapping joint that is not tapered. In some embodiments, ends 264/266 can be configured to interlock. Ends 264/266 may interlock in a number of manners such as by including mechanical interlocking features, such as bulbous structures, grooves, ridges, roughened surfaces, etc. Collectively, FIGS. 3-6 illustrate that the precise connection between proximal and distal sections 26/28 can vary to include any suitable arrangement.

Figure 7:
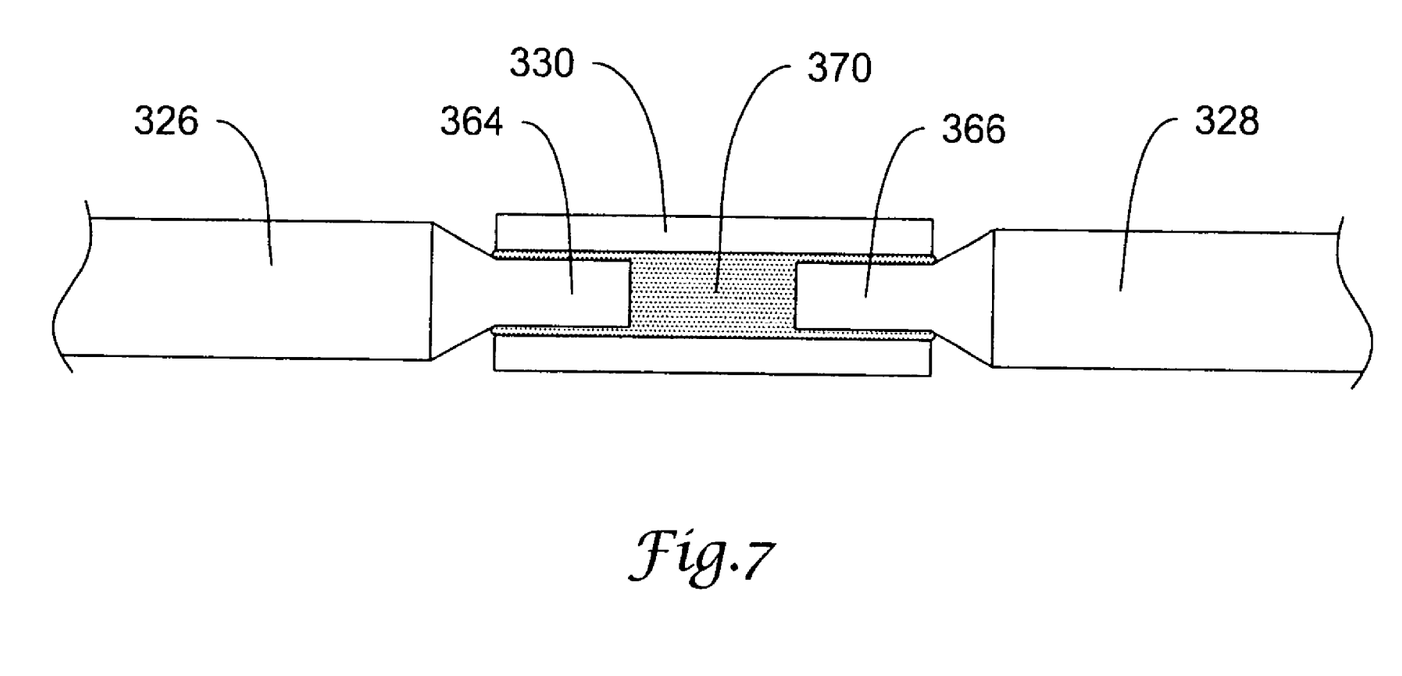
FIG. 7 is another cross-sectional view of the connection of a proximal section and distal section of an example filter wire.

FIG. 7 illustrates another example connection that may include a connector 330, a connector material 370, or both to secure ends 364/366 of proximal and distal sections 326/328. One example connector material 370 comprises a bismuth alloy. Some further discussion on the use of bismuth alloys can be found in U.S. patent application Ser. No. 10/375,766 entitled "Composite Medical Device", filed on Feb. 26, 2003, which is incorporated herein by reference. The bismuth alloy connector materials, for example connector material 370, for use in making the connection are adapted and configured to have the characteristic of expansion or growth upon or after solidification. In at least some embodiments, although normal thermal shrinkage of the liquid bismuth alloy may take place during cooling of the liquid, the crystalline structure that forms during solidification occupies a larger volume than the same mass of liquid. When the bismuth alloy connector material 370 are confined within a predetermined space, for example within an opening in a connector structure, compressive forces are generated as the alloy solidifies and expands or grows within the space.

Some examples of suitable bismuth alloy connector materials 370 include alloys of bismuth including additional alloying elements such as tin, indium, cadmium, lead, and the like. Due to the fact that the final medical device will make contact with or be inserted into a living body, in some embodiments, the alloy should include only elements that are known to be acceptable for contact with the body. For example, bismuth alloys including elements such as tin, indium, or the like, may be more acceptable for contact with the body. Some example alloys can include in the range of about 4 to about 80 wt. % bismuth, with the remainder being other alloying elements. Some examples of suitable alloys, and example ranges of wt. % of components within some alloys, and some specific examples of such alloys, include those having the ranges of components as illustrated in Table 1 as follows:

TABLE 1

| Type of alloy: | Range of components in some embodiments: | One example of a specific alloy falling within these ranges: |
|---|---|---|
| Bismuth-Tin alloy | 35 to 45 wt. % Bi, and 55 to 65 wt. % Sn | 40 wt. 60 wt. % Sn |
| Bismuth-Tin alloy | 53 to 63 wt. % Bi, and 37 to 47 wt. % Sn | 58 wt. % Bi, and 42 wt. % Sn |
| Bismuth-Indium alloy | 2 to 10 wt. % Bi, and 90 to 98 wt. % In | 5 wt. % Bi, and 95 wt. % In |
| Bismuth-Indium alloy | 62 to 72 wt. % Bi, and 28 to 38 wt. % In | 67 wt. % Bi, and 33 wt. % In |
| Bismuth-Indium alloy | 29 to 39% Bi, and 61 to 71 wt. % In | 34 wt. % Bi, and 66 wt. % In |
| Bismuth-Indium-Tin alloy | 53 to 63 wt. % Bi, 20 to 30 wt. % In, and 12 to 22 wt. % Sn | wt. % Bi, wt. % In, and wt. % Sn |

At least some of the bismuth alloy that can be used as the connector material 370 is characterized by relatively low melting temperatures compared to some other metal alloys. For example, in some embodiments, the bismuth alloy used is characterized as being a "fusible" alloy, meaning that it has a melting point in the range of about 50° C. to about 260° C. In some embodiments, the alloy has a melting point in the range of about 200° C. or below, or in the range of about 150° C. or below. In some embodiments, the alloy used is the eutectic alloy for the particular type of alloy being used, meaning that it is the particular alloy having the lowest melting point (i.e. eutectic point) that is obtainable by varying the proportions of the components of the alloy. Eutectic alloys have definite and minimum melting points in contrast to other combinations of the same metals. For such eutectic alloys, the minimum melting points as given above would be the eutectic melting point.

The low melting temperatures can be useful when connector material 370 is used in conjunction with structural elements that are made of or include temperature sensitive material. For example, some nickel-titanium alloys are annealed or shape set by exposure to higher temperatures. Therefore, the use of alloys having a lower temperature melting point can help to preserve the desired heat-treat state of structures made of such nickel-titanium alloys that need to be connected to other structures.

Referring to FIG. 7, the ends 364/366 of proximal and distal sections 326/328 and the bismuth alloy connector material 370 are disposed within the lumen defined in connector 330 in such a manner that the bismuth alloy connector material 370 solidifies and expands to exert a compressive force within the lumen. The compressive force within the lumen acts to connect connector 330 to ends 364/366 of proximal and distal sections 326/328, and thereby connect the proximal and distal sections 326/328 to each other. The ends 364/368 of proximal and distal sections 326/328 and the bismuth alloy connector material 370 can be disposed within the lumen of connector 330 using any suitable process or method that allows for such a connection to be formed. For example, in some embodiments, a sufficient amount of the bismuth alloy connector material 370 is applied to either one or both ends 364/366 and bismuth alloy connector material 370 is allowed to solidify. The bismuth alloy connector material 370 can be applied to the ends 364/366 using any suitable process, for example, a hot dipping process, a coating process, a spraying process, a plating process, or the like. Ends 364/366 are then inserted into the lumen within connector 330 until a dimensional interference is created. The bismuth alloy connector material 370 is then heated above its melting point of the bismuth alloy connector material 370, and an additional insertion force is applied to sections 326/328 to provide axial movement of the ends 364/366 further into the connector structure and into a bonding position. For example, the distal end 364 of the proximal section 326 and proximal end 366 of distal section 328 can be positioned adjacent one another in an overlapping or an end-to-end arrangement within connector 330, for example, like the embodiments shown in FIGS. 4-7. In some embodiments, ends 364/366 are moved into the bonding position, some excess bismuth alloy connector material 370 may be displaced from within the lumen in connector 330, indicating that the opening or lumen if full to capacity. The bismuth alloy connector material 370 is allowed to cool and solidify within the lumen. As the bismuth alloy connector material solidifies 370, it expands to exert a compressive force within the lumen. The compressive force within the lumen acts to provide a mechanical interlock between connector 330 to ends 364/366 of proximal and distal sections 326/328, and thereby connect the proximal and distal sections 326/328 to each other. In most cases, a permanent connection (as opposed to a releasable connection) is made. However, due to the nature of the bismuth alloy connector material, the joint can be disconnected, or reworked by reheating the connector material and separating or reworking the components of the joint.

Additionally, in some embodiments, as a result of the bismuth alloy expansion within the lumen, there may be a slight amount of outward motion of the sections 326/328 from the lumen of connector 330. In some embodiments, since the amount of expansion is very predictable and consistent, the wire components can be sized appropriately to compensate for this. Additionally, the bismuth alloy that may solidify outside of connector 330 can serve to form or function as strain relief just proximal and distal of connector 330. In some embodiments, bismuth alloy that may solidify outside of connector 330 may have or be worked to have a constant diameter, which can be beneficial for strain relief.

Once connected, connector 330 and proximal and distal sections 326/328 can be worked or formed to provide desired characteristics, such as shape or flexibility characteristics. For example, connector 330 and proximal and distal sections 326/328 can be worked, for example, by centerless grinding to provide a smooth and uniform profile across.

Figure 8:
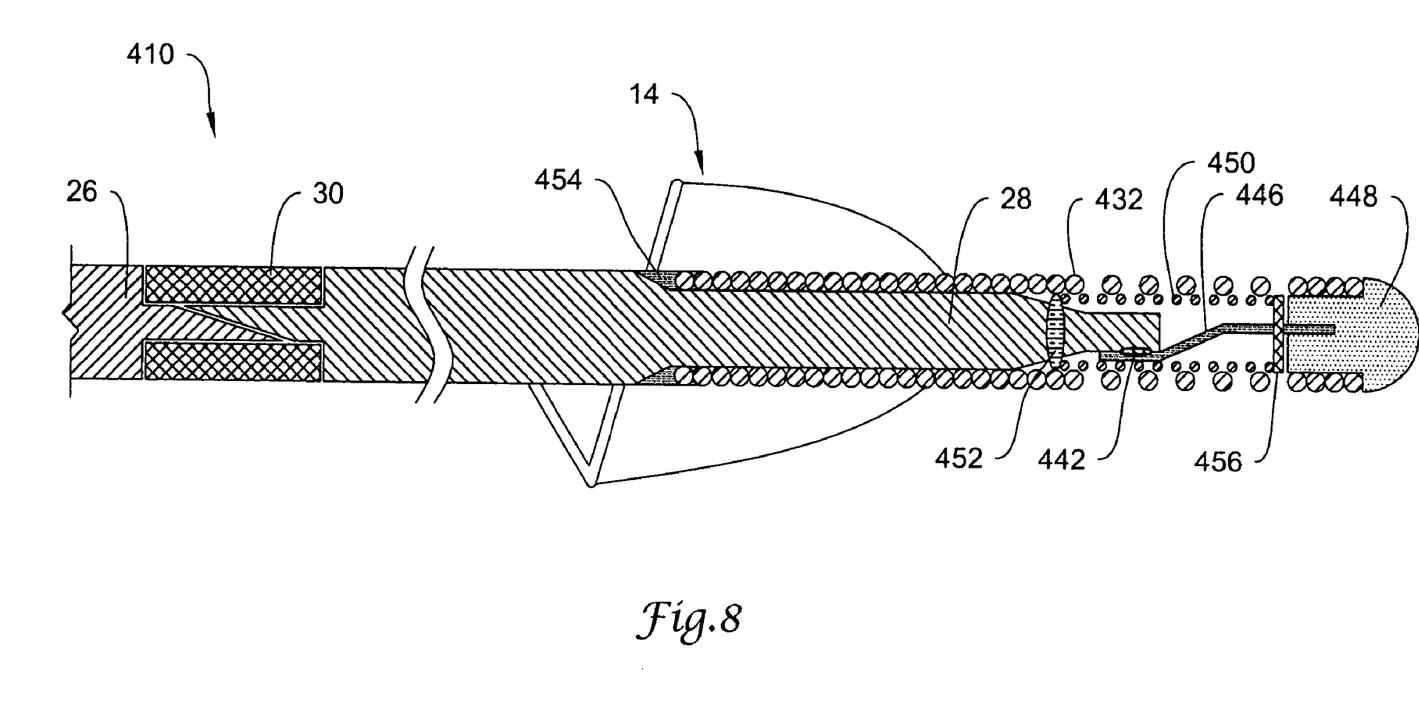
FIG. 8 is a partial cross-sectional view of another example medical device.

FIG. 8 depicts device 410 that is similar to device 10 except that covering 432 includes a coil. The proximal end of coil 432 may be attached to distal section 28 at an attachment point 454 using any suitable attachment technique, for example soldering, brazing, welding, adhesive bonding, crimping, or the like. The distal end of coil 432 is attached to ribbon 446 via a rounded tip portion 448. Rounded tip portion 448 can be made of any suitable material, for example a solder tip, a polymer tip, and the like.

Coil 432 may be made of a variety of materials including metals, metal alloys, polymers, and the like. Some examples of material for use in the coil include stainless steel, nickel-chromium alloy, nickel-chromium-iron alloy, cobalt alloy, or other suitable materials. Some additional examples of suitable material include straightened super elastic or linear elastic alloy (e.g., nickel-titanium) wire, or alternatively, a polymer material, such as a high performance polymer. In some embodiments, coil 432 can be made of a radiopaque materials such as gold, platinum, tungsten, or the like, or alloys thereof. Additionally, in some embodiments, a coating, for example a lubricious (e.g., hydrophylic) or other type of coating similar to that discussed above may be applied over portions or all of coil 432, or other portions of device 410.

Coil 432 may be formed of round or flat ribbon ranging in dimensions to achieve the desired flexibility. In some embodiments, coil 432 may be a round ribbon in the range of about 0.001-0.015 inches in diameter, and can have a length in the range of about 2 to about 4 inches, or more or less. Coil 432 can be wrapped in a helical fashion by conventional winding techniques. The pitch of adjacent turns of coil 432 may be tightly wrapped so that each turn touches the succeeding turn or the pitch may be set such that coil 432 is wrapped in an open fashion. In the embodiment shown, coil 432 is wrapped such that coil 432 has an open wrap at its proximal end, and includes a tightly wrapped portion adjacent tip 448.

As also seen in FIG. 8, device 410 may include an inner coil 450 disposed about a portion of distal section 28. Inner coil 450 may be coupled to distal section 28 at attachment point 452 using any suitable attachment technique, for example soldering, brazing, welding, adhesive bonding, crimping, or the like. The distal end of inner coil 450 may remain unattached, may be attached directly to the core, or may be attached to a spacer element 456 as shown. Spacer element 456 may be disposed about ribbon 146, and can be made of any suitable material, for example metal, metal alloy, or a polymer, or the like. In some embodiments, spacer 456 is made of a polymer such as polytetrafluroethylene (PTFE).

Inner coil 450 can be made of the same materials, and have the same general construction and pitch spacing as discussed above with regard to coil 432 or it may be different. In some embodiments, inner coil 450 is made of a radiopaque wire having a diameter less than that of the wire used to make the outer coil 432. It will be understood by those of skill in the art and others that a broad variety of materials, dimensions, and structures can be used to construct suitable embodiments, depending upon the desired characteristics.

FIG. 9 depicts another example device 510 that demonstrates that additional connectors may be used in the construction of shafts. Device 510 is similar to other devices described herein except that it includes a second connector 558 connecting a first and second portion 560/562 of distal region 528. Second connector 558 may be disposed distally of connector 530, which connects proximal section 526 to distal section 528. However, second connector 558 may be disposed at any suitable location. Moreover, additional connectors may also be included to connect various sections of device 510.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filtering device, comprising:
   a filter wire including a core member and a covering disposed over at least a portion of the core member, the core member including a proximal portion and a distal portion, the proximal portion having a first flexibility and including a distal end, the distal portion having a second flexibility different from the first flexibility and including a proximal end;
   a connector disposed over the distal end of the proximal portion and the proximal end of the distal portion, the connector fixedly secured to each of the proximal and distal portions of the core member; and
   a filter assembly coupled to the filter wire, the filter assembly including a filter frame, a filter membrane coupled to the filter frame, and one or more struts extending between the filter frame and the filter wire.

2. The filtering device of claim 1, wherein the proximal portion comprises stainless steel.

3. The filtering device of claim 1, wherein the distal portion comprises nickel-titanium alloy.

4. The filtering device of claim 1, wherein the connector comprises a connector material that is compatible for bonding to both the proximal and distal portions.

5. The filtering device of claim 4, wherein the connector material comprises a nickel-chromium alloy.

6. The filtering device of claim 1, wherein a reduced cross sectional area is defined adjacent at least one of the distal end of the proximal portion and the proximal end of the distal portion.

7. The filtering device of claim 6, wherein the reduced size region or regions include a taper.

8. The filtering device of claim 6, wherein both the proximal portion and the distal portion include a reduced size region, and wherein the reduced size region of the proximal portion and the reduced size region of the distal portion overlap.

9. The filtering device of claim 6, wherein both the proximal portion and the distal portion include a reduced size region, and wherein the reduced size region of the proximal portion and the reduced size region of the distal portion have interlocking shapes.

10. The filtering device of claim 6, wherein both the proximal portion and the distal portion include a reduced cross sectional area, and wherein the reduced cross sectional area of the proximal portion and the reduced cross sectional area of the distal portion are joined together to define a butt joint.

11. The filtering device of claim 1, wherein the covering comprises a polymer sheath.

12. The filtering device of claim 1, wherein the covering comprises a coil.

13. The filtering device of claim 1, wherein the distal region of the core member include a first section and a second section that are connected by a second connector.

14. The filtering device of claim 1, further comprising a bismuth alloy connector material disposed adjacent the distal end of the proximal portion and the proximal end of the distal portion.

15. The filtering device of claim 1, wherein the connector is welded to the proximal portion and to the distal portion.

* * * * *